(12) United States Patent
Matsushita et al.

(10) Patent No.: US 12,100,144 B2
(45) Date of Patent: Sep. 24, 2024

(54) METHOD AND SYSTEM FOR CELL ISOLATION ASSISTANCE AND COMPUTER-READABLE MEDIUM

(71) Applicant: EVIDENT CORPORATION, Nagano (JP)

(72) Inventors: Akira Matsushita, Tokyo (JP); Yu Hirosawa, Tokyo (JP); Taiji Mine, Tokyo (JP)

(73) Assignee: Evident Corporation, Nagano (JP)

( * ) Notice: Subject to any disclaimer, the term of this patent is extended or adjusted under 35 U.S.C. 154(b) by 357 days.

(21) Appl. No.: 17/668,501

(22) Filed: Feb. 10, 2022

(65) Prior Publication Data

US 2022/0164956 A1 May 26, 2022

Related U.S. Application Data

(63) Continuation of application No. PCT/JP2019/040401, filed on Oct. 15, 2019.

(51) Int. Cl.
*G06T 7/12* (2017.01)
*G06T 7/00* (2017.01)

(52) U.S. Cl.
CPC .... *G06T 7/0012* (2013.01); *G06T 2207/30024* (2013.01)

(58) Field of Classification Search
CPC .............. G06T 7/0012; G06T 2207/30024
USPC ....................................................... 382/128
See application file for complete search history.

(56) References Cited

U.S. PATENT DOCUMENTS

| 2007/0041904 A1* | 2/2007 | Jiang ................. A61K 49/0056 435/456 |
| 2013/0143315 A1 | 6/2013 | Yamamoto |
| 2015/0216905 A1 | 8/2015 | Kreke et al. |
| 2018/0021380 A1* | 1/2018 | Han ..................... A61K 31/728 424/93.7 |
| 2019/0095692 A1* | 3/2019 | Nakatomi ............. G06V 20/698 |

FOREIGN PATENT DOCUMENTS

| JP | 2004-344007 A | 12/2004 |
| JP | 2008-212021 A | 9/2008 |
| JP | 2015-521054 A | 7/2015 |
| JP | 2016-116461 A | 6/2016 |
| JP | 2019-058156 A | 4/2019 |
| WO | 2012-015030 A1 | 2/2012 |
| WO | 2018-101004 A1 | 6/2018 |
| WO | 2019-163304 A1 | 8/2019 |

OTHER PUBLICATIONS

International Search Report dated Dec. 24, 2019 issued in PCT/JP2019/040401.

* cited by examiner

*Primary Examiner* — Michael R Neff
(74) *Attorney, Agent, or Firm* — Scully, Scott, Murphy & Presser, P.C.

(57) ABSTRACT

A method for assisting in cell isolation from a biological tissue section includes: obtaining cell images that are each an image of cells isolated from the biological tissue section, the biological tissue section being soaked in a solution containing an enzyme; calculating, from the cell images, a number of the cells isolated from the biological tissue section as an indicator of the cell isolation from the biological tissue section; and visualizing a temporal change in the indicator on the basis of a history of the indicator.

26 Claims, 16 Drawing Sheets

METHOD AND SYSTEM FOR CELL ISOLATION ASSISTANCE AND COMPUTER-READABLE MEDIUM

CROSS REFERENCE TO RELATED APPLICATIONS

This application is based upon and claims the benefit of priority to PCT Application No. PCT/JP2019/040401, filed on Oct. 15, 2019, the entire contents of which are incorporated herein by reference.

This is a Continuation Application of PCT Application No. PCT/JP2019/040401, filed on Oct. 15, 2019, which was not published under PCT Article 21(2) in English.

TECHNICAL FIELD

Disclosures herein are related to a method and system for cell isolation assistance, and a computer-readable medium.

BACKGROUND

With respect to the cultivation of cells included in biological tissues such as cartilage or skin, cells need to be isolated from a biological tissue section obtained from an organism. For example, cell isolation may be performed by soaking a biological tissue section in a solution containing a proteolytic enzyme such as collagenase or trypsin. Such a method is described in, for example, Japanese Laid-open Patent Publication No. 2004-344007.

Japanese Laid-open Patent Publication No. 2004-344007 describes, as an example of a desirable condition for cell isolation, the process of soaking cells in a solution having a trypsin concentration of 1 mg/ml at 37° C. for 40 minutes.

SUMMARY

A method in accordance with an aspect of the present invention is a method for assisting in cell isolation from a biological tissue section and includes: obtaining cell images that are each an image of cells isolated from the biological tissue section, the biological tissue section being soaked in a solution containing an enzyme; calculating, from the cell images, a number of the cells isolated from the biological tissue section as an indicator of the cell isolation from the biological tissue section; and visualizing a temporal change in the indicator on the basis of a history of the indicator.

A method in accordance with another aspect of the present invention is a method for assisting in cell isolation from a biological tissue section and includes: obtaining cell images that are each an image of cells isolated from the biological tissue section, the biological tissue section being soaked in a solution containing an enzyme; calculating, from the cell images, a contrast of the cell images as an indicator of the cell isolation from the biological tissue section; and visualizing a temporal change in the indicator on the basis of a history of the indicator.

A system in accordance with an aspect of the present invention includes: an image capturing apparatus that images a biological tissue section soaked in a solution containing an enzyme; and a control apparatus that obtains, from the image capturing apparatus, cell images that are each an image of cells isolated from the biological tissue section, wherein the control apparatus calculates, from the obtained cell images, a number of the cells isolated from the biological tissue section as an indicator of cell isolation from the biological tissue section, and visualizes a temporal change in the calculated indicator on the basis of a history of the indicator.

A system in accordance with another aspect of the present invention includes: an image capturing apparatus that images a biological tissue section soaked in a solution containing an enzyme; and a control apparatus that obtains, from the image capturing apparatus, cell images that are each an image of cells isolated from the biological tissue section, wherein the control apparatus calculates, from the obtained cell images, a contrast of the cell images as an indicator of cell isolation from the biological tissue section, and visualizes a temporal change in the calculated indicator on the basis of a history of the indicator.

A computer-readable medium in accordance with an aspect of the present invention is a non-transitory computer-readable medium having a program recorded therein, the program causing a computer to perform a process for: obtaining cell images that are each an image of cells isolated from a biological tissue section soaked in a solution containing an enzyme; calculating, from the obtained cell images, a number of the cells isolated from the biological tissue section as an indicator of the cell isolation from the biological tissue section; and visualizing a temporal change in the calculated indicator on the basis of a history of the indicator.

A computer-readable medium in accordance with an aspect of the present invention is a non-transitory computer-readable medium having a program recorded therein, the program causing a computer to perform a process for: obtaining cell images that are each an image of cells isolated from a biological tissue section soaked in a solution containing an enzyme; calculating, from the obtained cell images, a contrast of the cell images as an indicator of cell isolation from the biological tissue section; and visualizing a temporal change in the calculated indicator on the basis of a history of the indicator.

DESCRIPTION OF EMBODIMENTS

The time required for cell isolation is expected to vary according to various conditions, e.g., the size, mass, shape, or type of a biological tissue section. It will be difficult to determine these conditions in advance. In this regard, the desirable conditions for cell isolation described in Japanese Laid-open Patent Publication No. 2004-344007 are nothing but ones that were empirically found by operators. A long estimated time that was obtained to prioritize reliable completion of cell isolation may possibly be described as a desirable condition.

Soaking cells in a proteolytic enzyme for an unnecessarily long time will damage the cells. Excessively damaging the cells will adversely affect later cultivation and is thus undesirable.

The following describes embodiments of the present invention.

Figure 1:
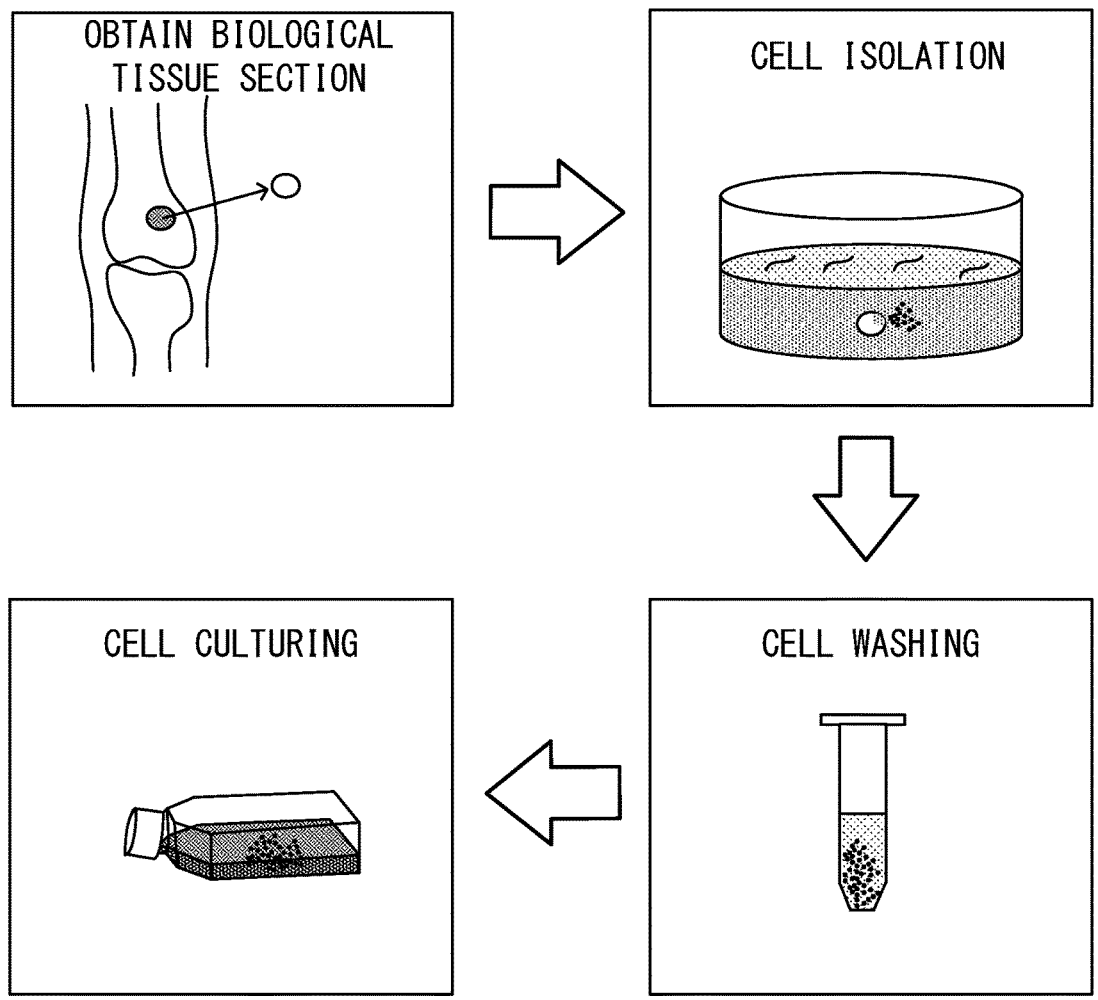
FIG. 1 is an explanatory diagram for a procedure for preparing culture cells.

FIG. 1 is an explanatory diagram for a procedure for preparing culture cells. As depicted in FIG. 1, starting cell culturing involves a plurality of steps, e.g., a step for obtaining a biological tissue section from an organism, a step for isolating cells from the biological tissue section, a step for washing and extracting the isolated cells.

For example, in the step for obtaining a biological tissue section from an organism, the biological tissue section may be obtained from the organism and cut into pieces having a predetermined size. In the process for isolating cells from the biological tissue section, pieces obtained from the cutting are soaked in a solution containing a proteolytic enzyme with the concentration thereof adjusted in advance, and the result is disposed in an incubator with a managed environmental temperature. In the next step for washing and extracting isolated cells, cells isolated from the biological tissue section are extracted by separating the same from other materials by using, for example, a centrifugal separator. The number of extracted cells is counted by causing the cells to pass through, for example, a flow cell meter. Afterward, the cells are cultured as culture cells.

To successfully perform the cell culturing, it is important to appropriately deal with cells in each of the steps performed before the culturing starts. The following describes a method for appropriately isolating cells, with attention focused on the step for isolating the cells, among the above steps.

Figure 2:
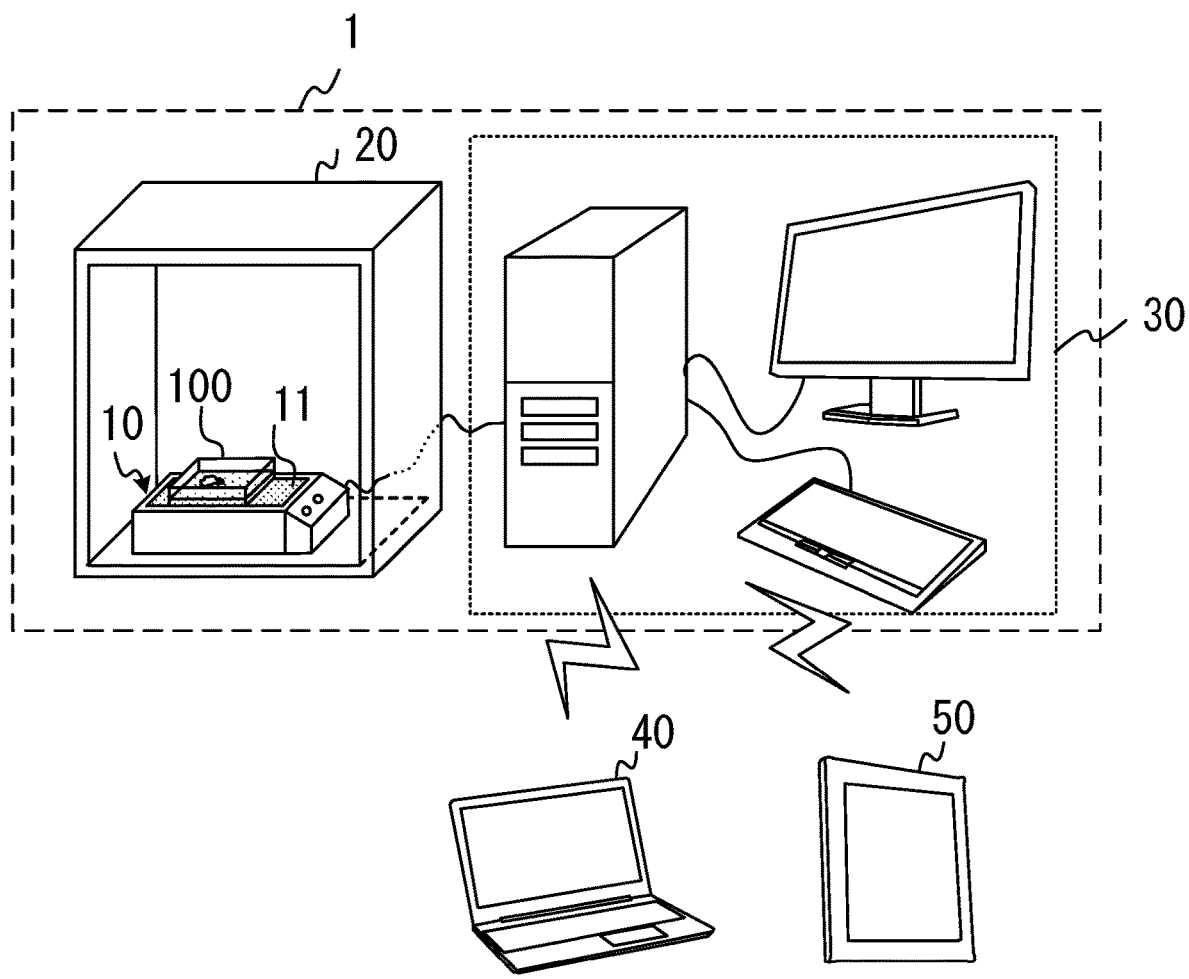
FIG. 2 exemplifies the configuration of a cell isolation assistance system.
Figure 3:
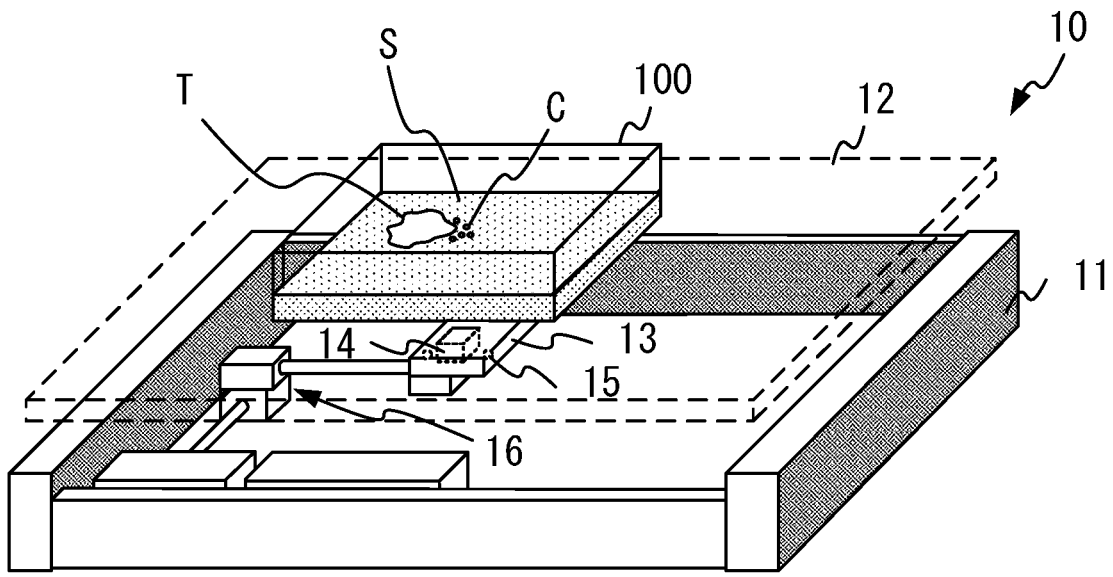
FIG. 3 exemplifies the configuration of an image capturing apparatus.
Figure 4:
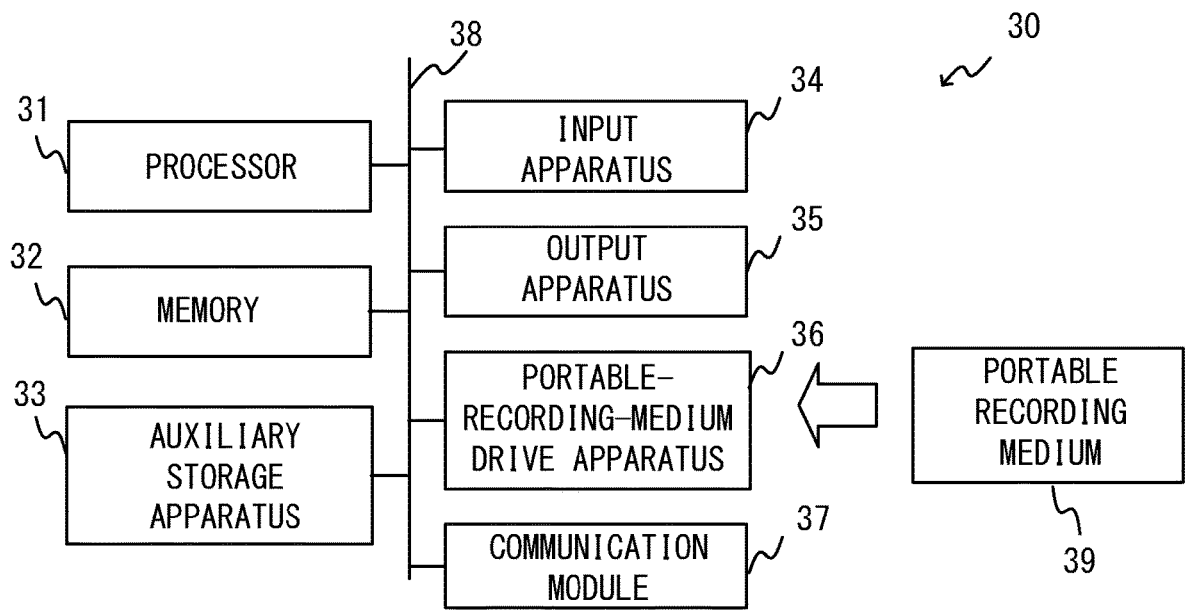
FIG. 4 exemplifies the configuration of a control apparatus.

FIG. 2 exemplifies the configuration of a cell isolation assistance system. FIG. 3 exemplifies the configuration of an image capturing apparatus. FIG. 4 exemplifies the configuration of a control apparatus. Descriptions are given in the following of the configuration of a system 1 depicted in FIG. 2 by referring to FIGS. 2-4.

The system 1 assists in cell isolation. As depicted in FIG. 2, the system 1 includes an image capturing apparatus 10 placed within an incubator 20, and a control apparatus 30. In the system 1, the control apparatus 30 calculates, on the basis of an image generated by the image capturing apparatus 10, information that constitutes an indicator of cell isolation, visualizes a change in the information, and provides the visualized change for the user. The control apparatus 30 communicates with the image capturing apparatus 10 and client terminals (client terminals 40 and 50). The system 1 may include the incubator 20 and a client terminal.

As depicted in FIG. 2, a container 100 is placed on the image capturing apparatus 10 accommodated within the incubator 20. For example, the container 100 may be, but is not particularly limited to, a petri dish, a flask, or a microplate.

As indicated in FIG. 3, the container 100 accommodates a biological tissue section T soaked in a solution S containing a proteolytic enzyme. The proteolytic enzyme may be, but is not particularly limited to, collagenase or trypsin. For example, the biological tissue section T may be, but is not particularly limited to, human cartilage or skin. Soaking the biological tissue section T in the solution S containing the proteolytic enzyme causes cells C to be gradually isolated from the biological tissue section T. Isolation of cells C from the biological tissue section T that occurs due to an action of the proteolytic enzyme may be referred to as digestion.

The image capturing apparatus 10 images the cells isolated from the biological tissue section T accommodated within the container 100 so as to generate cell images that are each an image of the cells isolated from the biological tissue section T. Furthermore, the image capturing apparatus 10 transmits the generated cell images to the control apparatus 30. The image capturing apparatus 10 and the control apparatus 30 may communicate with each other wirelessly or by a wired link.

More specifically, as depicted in FIG. 3, the image capturing apparatus 10 includes a housing 11 and a stage 12 on which the container 100 is placed. The image capturing apparatus 10 also includes an image capturing unit 13 and a moving mechanism 16 for moving the image capturing unit 13, both of which are positioned within the housing 11 and below the stage 12. The image capturing unit 13 is provided with an image pickup element 14, light sources 15, and an optical system (not illustrated).

For example, the image pickup element 14 may be a charge-coupled-device (CCD) image sensor, or a complementary-MOS (CMOS) image sensor. The light sources 15 are, for example, light emitting diodes (LEDs) and illuminate the container 100 from below the stage 12. The light sources 15 may be placed opposite to each other with the image pickup element 14 therebetween. For example, the light sources 15 may each selectively emit light having a wavelength corresponding to red (R), green (G), or blue (B) by switching between the wavelengths corresponding to the three colors of red (R), green (G), and blue (B), or may emit white light. Red (R) light, which has a long wavelength, is desirably used to reduce damage to cells. In the image capturing apparatus 10, light emitted from a light source 15 passes through the bottom surface of the container 100, and a portion of light reflected by the upper surface of the container 100 passes through the cells C isolated from the biological tissue section T within the container 100. By using the light that has passed through the cells C isolated from the biological tissue section T within the container 100, the optical system forms an optical image of the cells C on the image pickup element 14.

For example, the moving mechanism 16 may include a drive source such as a motor and move the image capturing unit 13 in a direction orthogonal to the optical axis of the optical system (in an XY direction). The moving mechanism 16 moves the image capturing unit 13 in the XY direction, thereby allowing the image capturing apparatus 10 to change the range of image capturing. The moving mechanism 16 may also move the image capturing unit 13 in the direction of the optical axis of the optical system (Z direction). The image capturing apparatus 10 may adjust a focus position by using the moving mechanism 16. Alternatively, the image capturing apparatus 10 may adjust the focus position by moving at least one lens among lenses included in the optical system in the direction of the optical axis.

The control apparatus 30 is a computer that controls the system 1. As depicted in FIG. 4, the control apparatus 30 includes a processor 31, a memory 32, an auxiliary storage apparatus 33, an input apparatus 34, an output apparatus 35, a portable-recording-medium drive apparatus 36 for driving a portable recording medium 39, a communication module 37, and a bus 38. The auxiliary storage apparatus 33 and the portable recording medium 39 are each an example of a non-transitory computer-readable recording medium storing a program.

For example, the processor 31 may be any type of one or more processing circuits that include a central processing unit (CPU) and a graphics processing unit (GPU). The processor 31 performs programmed processing, such as a cell isolation assistance method (described hereinafter), by loading a program stored in the auxiliary storage apparatus 33 or the portable recording medium 39 into the memory 32 and then executing the loaded program.

For example, the memory 32 may be any semiconductor memory such as a random access memory (RAM). In program execution, the memory 32 functions as a work memory for storing a program or data stored in the auxiliary storage apparatus 33 or the portable recording medium 39. For example, the auxiliary storage apparatus 33 may be a nonvolatile memory such as a hard disk or a flash memory. The auxiliary storage apparatus 33 is used mainly to store various data and programs.

The portable-recording-medium drive apparatus 36 accommodates the portable recording medium 39. The portable-recording-medium drive apparatus 36 can output data stored in the memory 32 or the auxiliary storage apparatus 33 to the portable recording medium 39 and read a program, data, and the like from the portable recording medium 39. The portable recording medium 39 may be any recording medium that can be carried. For example, the portable recording medium 39 may include an SD card, a universal serial bus (USB) flash memory, a compact disc (CD), and a digital versatile disc (DVD).

The input apparatus 34 is, for example, a keyboard or a mouse. The output apparatus 35 is, for example, a display apparatus or a printer. For example, the communication module 37 may be a wire communication module that communicates with the image capturing apparatus 10, which is connected via an external port. The communication module 37 may also be a wireless communication module. The bus 38 connects the processor 30, the memory 32, the auxiliary storage apparatus 33, and the like to each other in a manner such that data can be communicated therebetween.

The configuration depicted in FIG. 4 is an example of the hardware configuration of the control apparatus 30. The control apparatus 30 is not limited to this configuration. The control apparatus 30 may be a general-purpose or special-purpose apparatus. For example, the control apparatus 30 may include a specifically designed electric circuit, e.g., an application specific integrated circuit (ASIC). The control apparatus 30 may be configured using a field-programmable gate array (FPGA).

The control apparatus 30 transmits an image capturing instruction to the image capturing apparatus 10. The control apparatus 30 receives a cell image generated by the image capturing apparatus 10 imaging cells C isolated from the biological tissue section T. In addition, the control apparatus 30 calculates, on the basis of a cell image obtained from the image capturing apparatus 10, information that constitutes an indicator of cell isolation from the biological tissue section T, visualizes a temporal change in the information, and provides the visualized temporal change for the user. In particular, for example, the control apparatus 30 may display, on a display apparatus constituted by the output apparatus 35, a screen including the visualized information.

The client terminal 40 is a notebook computer. The client terminal 50 is a tablet computer. The control apparatus 30 may output screen information to a client terminal (client terminal 40 or 50) at a request therefrom. As long as the client terminals include a display unit, the client terminals may be, for example, a desktop computer or a smartphone.

By using the image capturing apparatus 10 disposed within the incubator 20, the system 1 configured as described above can obtain, as image information, information on the process in which cells are isolated from a biological tissue section T, i.e., information that would be difficult to obtain according to the prior art. By using this feature, the system 1 assists in user tasks, such that cell isolation is appropriately performed.

Figure 5:
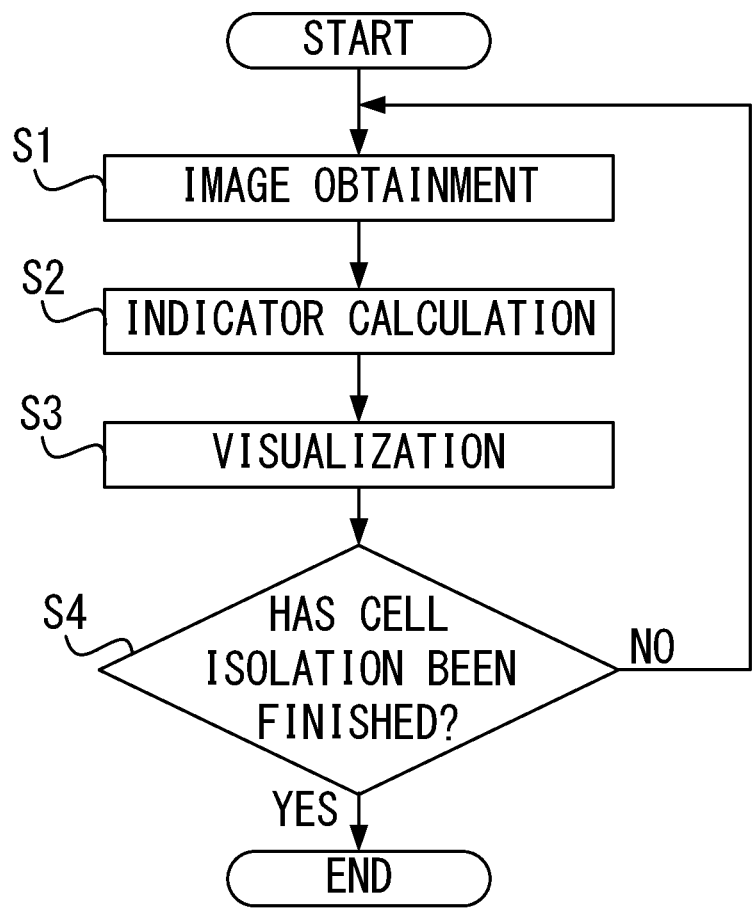
FIG. 5 is a flowchart illustrating an example of a method for assisting in isolating cells.
Figure 6:
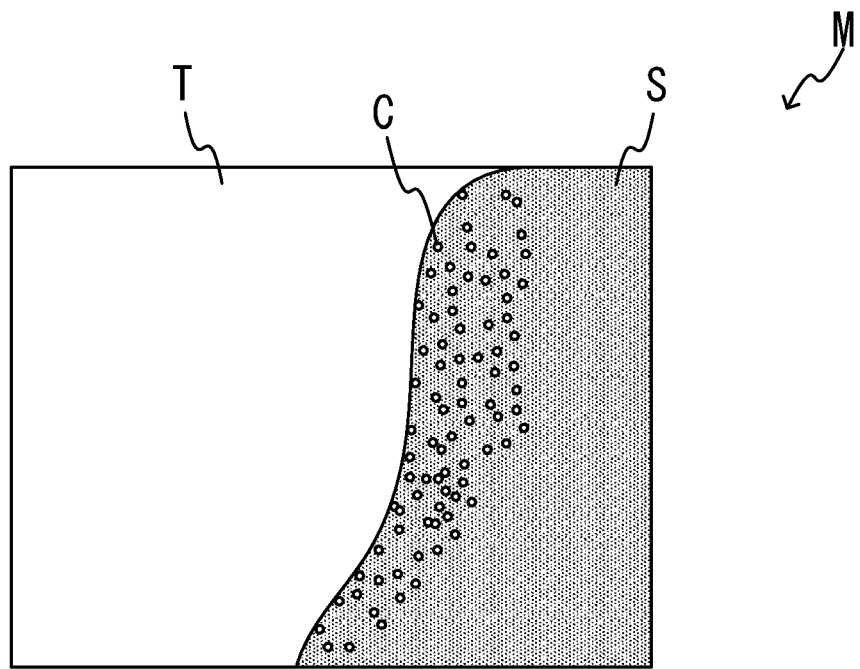
FIG. 6 illustrates an example of an image obtained by an image capturing apparatus.
Figure 7A:
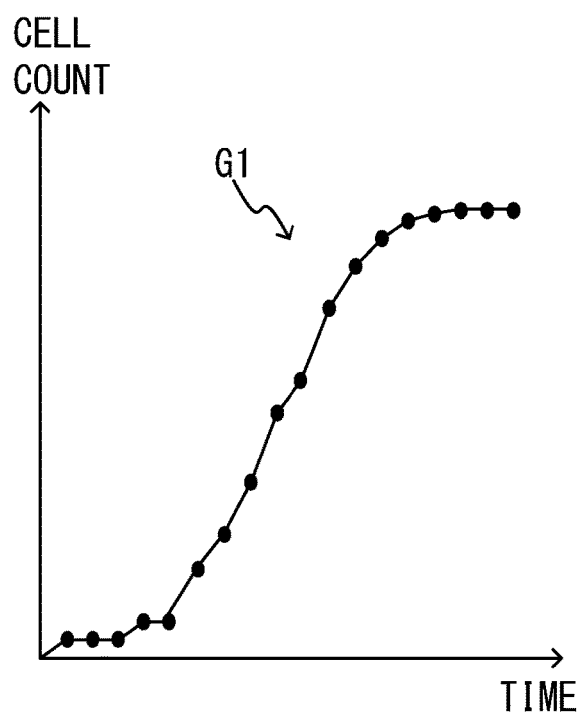
FIG. 7A is an example of a graph visualizing a change in a cell count.
Figure 7B:
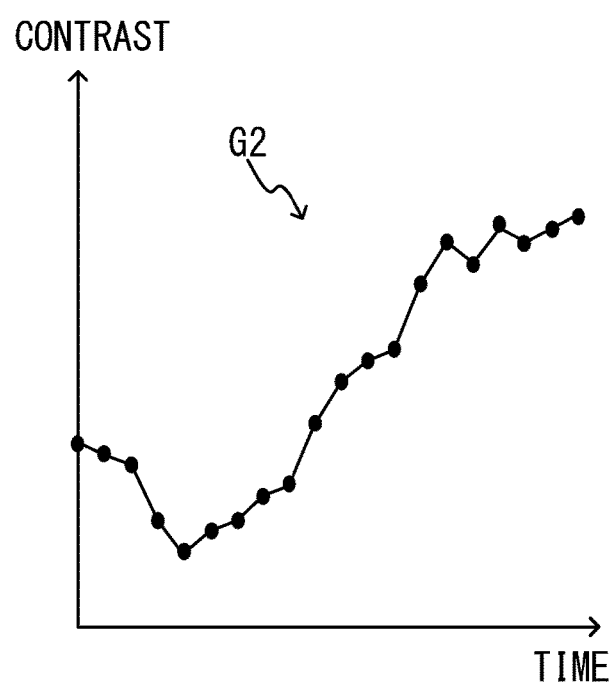
FIG. 7B is an example of a graph visualizing a change in a contrast.

FIG. 5 is a flowchart illustrating an example of a method for assisting in isolating cells. FIG. 6 illustrates an example of an image obtained by the image capturing apparatus. FIG. 7A is an example of a graph visualizing a change in a cell count. FIG. 7B is an example of a graph visualizing a change in a contrast. By referring to FIGS. 5, 6, 7A, and 7B, the following describes a method implemented by the system 1 for assisting in cell isolation from a biological tissue section (hereinafter simply referred to as the "cell isolation assistance method").

As indicated in FIG. 5, the cell isolation assistance method implemented by the system 1 includes three steps of image obtainment (step S1), indicator calculation (step S2), and visualization (step S3), and these steps are repeated until the cell isolation is finished (YES in step S4).

In the image obtainment step of step S1, the control apparatus 30 obtains an image generated by the image capturing apparatus 10 imaging cells isolated from a biological tissue section T soaked in a solution containing an enzyme. In the system 1, the control apparatus 30 controls the image capturing apparatus 10, which is disposed within the incubator 20 with the container 100 placed thereon, so that an image of cells isolated from the biological tissue section T can be obtained without the container 100 being taken out of the incubator 20. FIG. 6 indicates an image M obtained by the image capturing apparatus 10 imaging cells C leached in the solution S as time advances after being isolated from the biological tissue section T.

Without the biological tissue section T or the cells C being exposed to outside air and without the user touching the container 100, the system 1 can record, as an image, the process of the cells C being isolated from the biological tissue section T. Thus, the image obtainment step of step S1 allows information pertaining to cell isolation to be obtained while suppressing damage to cells C and suppressing a risk of occurrence of contamination.

The image obtainment step of step S1 has great advantages in comparison to when observation is performed using a microscope or the like with the container 100 being taken out of the incubator 20, in terms of the reduction in the task burden on the user owing to the unnecessity to take the container into or out of the incubator 20, and the cost reduction resulting from a reduction in the number of cells that are spoiled due to contamination, in addition to the quality of culture cells as described above.

In the indicator calculation step of step S2, the control apparatus 30 calculates an indicator of the cell isolation on the basis of the image obtained from the image capturing apparatus 10. An indicator of the progress of isolation of cells C from a biological tissue section T is not found in the prior art. One major reason for this is that in the prior art, there are no means for obtaining an image of the process of cells C being isolated from a biological tissue section T. By contrast, the system 1 can obtain an image of a cell isolation process by using the image capturing apparatus 10. Hence, an indicator of the cell isolation can be calculated on the basis of the image of the cell isolation process.

In the indicator calculation step of step S2, at least either a contrast or the number of cells isolated from the biological tissue section T is calculated from the image obtained in step S1 as an indicator of the cell isolation from the biological tissue section T. It will be more desirable that both the number of isolated cells and the contrast be calculated as indicators. Note that the contrast is the contrast of the cell image obtained by the image capturing apparatus 10. The contrast of the cell image may be the contrast of the entirety of the cell image or the contrast of a region of interest of the cell image determined in advance.

The number of isolated cells increases as the cell isolation from the biological tissue section T progresses, and converges to a certain number when the isolation is completed. Thus, the cell count exhibits a change such as that indicated in FIG. 7A in the cell isolation process. Meanwhile, the contrast decreases directly after the start of the cell isolation because the edge of the biological tissue section T loses sharpness due to the cell isolation, but increases as the isolation progresses because cells account for a larger proportion of the image and thus focus is brought into a wider region. In particular, as indicated in FIG. 7B, once isolation starts, the contrast temporarily decreases, then starts to increase, and finally converges approximately into a certain range when the isolation is completed. The change in the contrast occurs because the depth of field of the image capturing apparatus 10 is set in accordance with the cells C, which are thinner than the biological tissue section T.

The cell count and the contrast are preferable indicators of the cell isolation in that, as indicated in FIGS. 7A and 7B, both change as the cell isolation progresses and respectively converge to a certain number and into a certain range when the isolation is completed.

In the visualization step of step S3, temporal changes in the indicators calculated in step S2 are visualized on the basis of the history of the indicators. Note that the history of the indicators refers to a set of repeatedly calculated indicators corresponding to different times. In the visualization step of step S3, for example, the control apparatus 30 may display a graph indicating a temporal change in the indicator on the output apparatus 35 or a client terminal. The system 1 visualizes a temporal change in at least either the cell count or contrast calculated as an indicator of the cell isolation, so that the user can grasp the progress of the cell isolation from the quantitative information. In particular, displaying the graph indicating a temporal change in an indicator allows the user to more intuitively and easily grasp the progress of the cell isolation.

It is desirable to calculate both the cell count and the contrast as indicators in step S2. It is desirable to visualize a temporal change in both of the indicators in step S3.

The cell count is the number of cells isolated from the biological tissue section T and is thus quantitative. The cell count directly indicates the progress of the isolation and thus would be, as a general rule, an optimum indicator of the cell isolation. However, the cell count may vary irrespective of the cell isolation, due to, for example, cells flowing out of the field of view of the image capturing apparatus 10 or flowing into the field of view. It is desirable to calculate an indicator different from the cell count so that the progress of the cell isolation can be correctly evaluated even in such a situation.

The contrast is desirably used as the indicator different from the cell count. The contrast does not directly indicate, unlike the cell count, the cell isolation and thus does not have a uniform relationship (e.g., linear relationship) with the cell count. Using the contrast which does not have a uniform relationship with the cell count as an indicator together with the cell count allows the robustness of the indicators of the cell isolation to be enhanced. In particular, unlike the cell count, the contrast indicates a qualitative characteristic of the image, rather than a quantitative characteristic thereof, and thus does not tend to exhibit a variation resulting from the limited range of field of view. Accordingly, using the cell count as an indicator allows the progress of the isolation to be directly indicated in a quantitative manner, and using the contrast as an indicator allows the progress of the isolation to be indicated, with the influence of cell migration removed. Hence, the contrast is an excellent indicator that can be used together with the cell count, in that both the progress evaluation for the cell isolation that is based on the cell count and the progress evaluation for the cell isolation that is based on the contrast are unlikely to be concurrently unreliable.

As described above, by performing the processes depicted in FIG. 5, the system 1 can visualize information for evaluating the progress of cell isolation. In particular, by using both the cell count and the contrast as indicators of the cell isolation, information with high robustness can be provided for the user. The user can objectively perceive the progress of the cell isolation, in particular the completion of the cell isolation, from the information provided by the system 1. Thus, the user can perceive the completion of the cell isolation without relying on experience or instinct, so that the isolation step can be finished in a minimum necessary time. Accordingly, the system 1 does not take an unnecessarily long time for the isolation step and thus can reliably assist in cell isolation while suppressing damage to cells, thereby providing culture cells efficiently. Moreover, since the completion of cell isolation can be objectively perceived, any operator can provide culture cells of stable quality, thereby leading to the advantage of enhancing the reliability of an experiment or transplantation using the culture cells.

The following describes specific examples of the cell isolation assistance method implemented by the system 1.

First Embodiment

Figure 8:
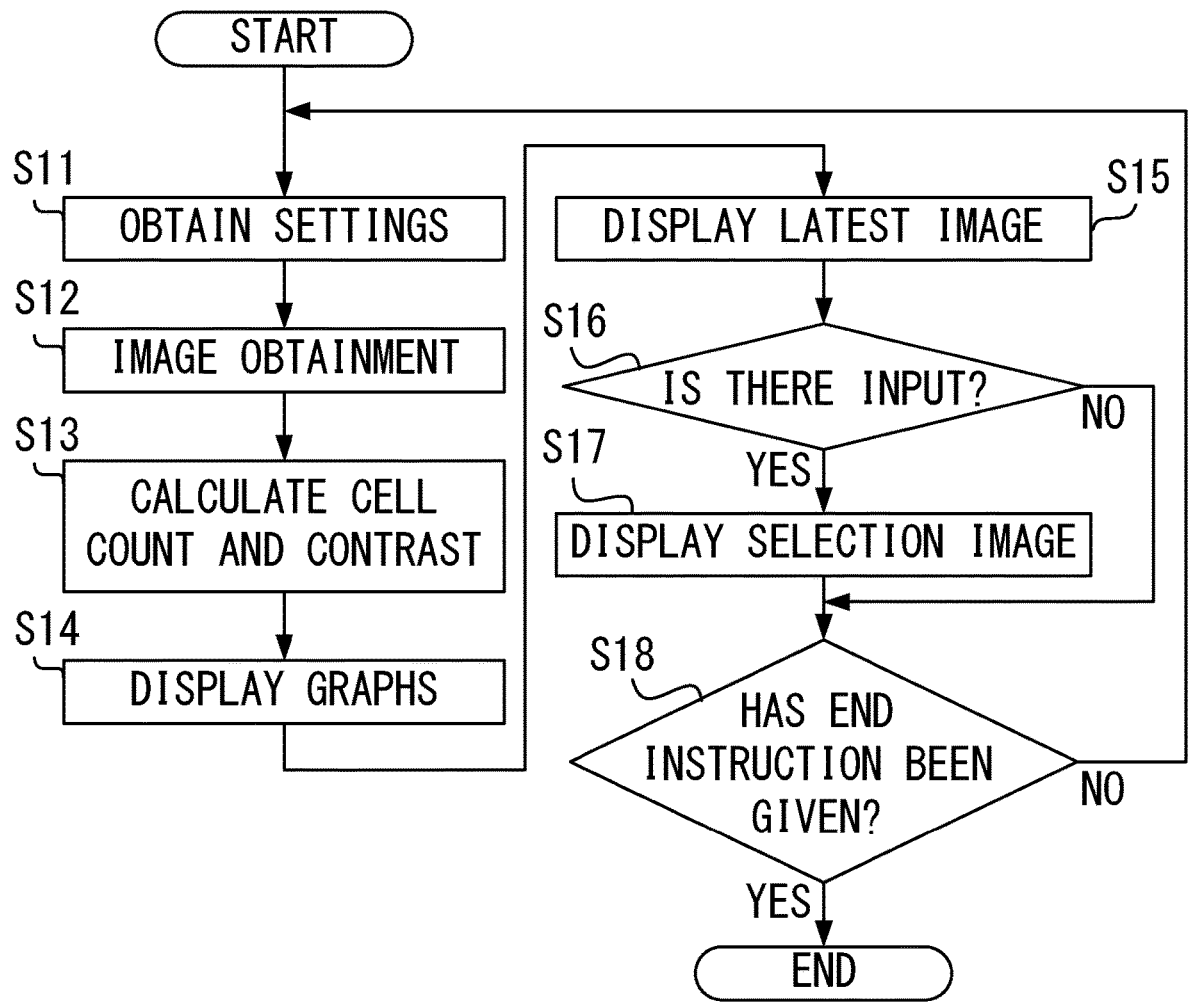
FIG. 8 is a flowchart for a cell isolation assistance method in accordance with a first embodiment.
Figure 9:
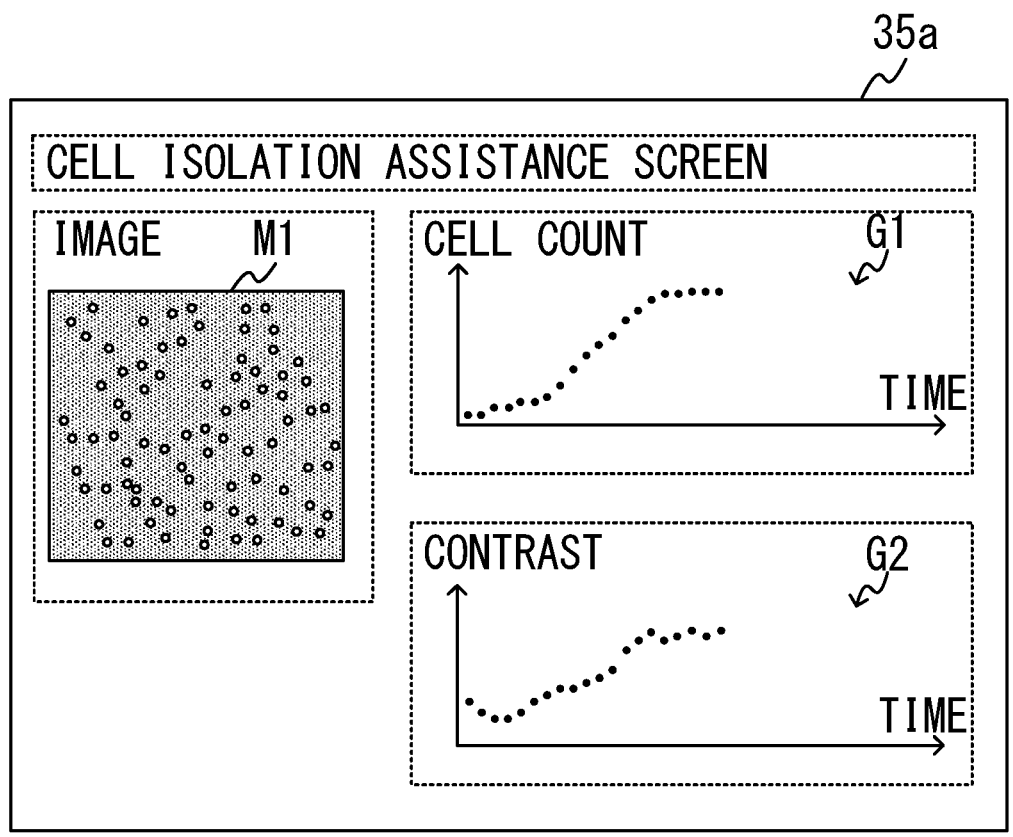
FIG. 9 illustrates an example of a screen displayed using a cell isolation assistance method in accordance with a first embodiment.
Figure 10:
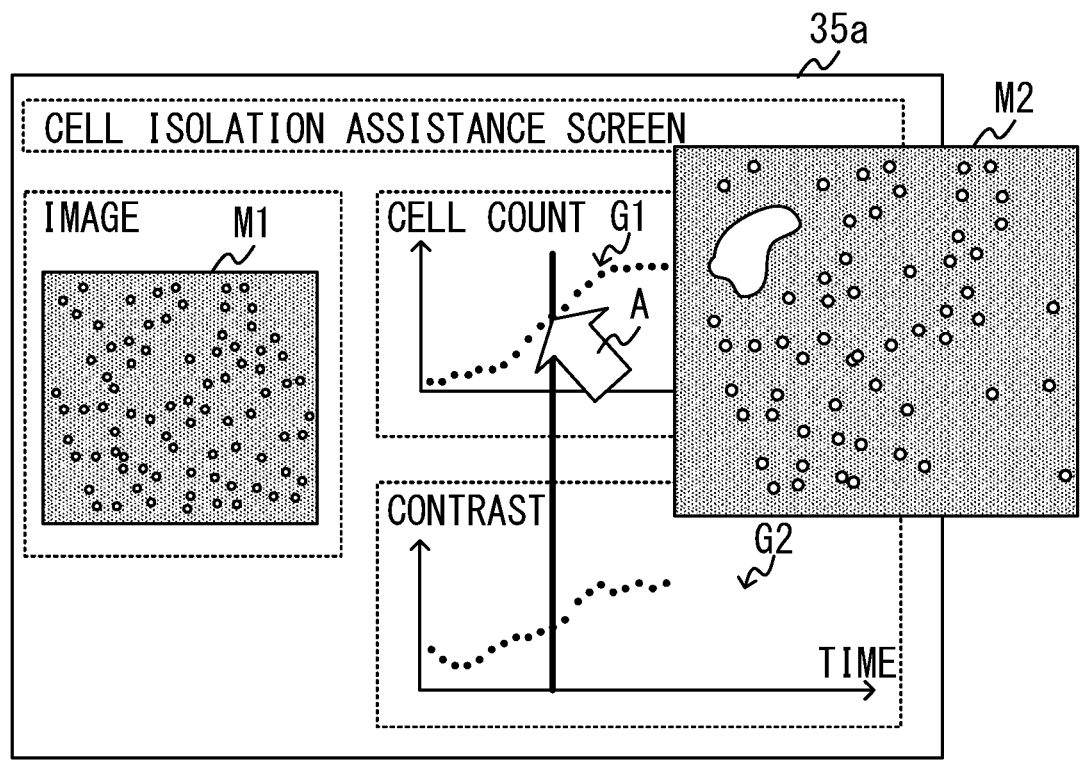
FIG. 10 illustrates another example of a screen displayed using a cell isolation assistance method in accordance with a first embodiment.

FIG. 8 is a flowchart for a cell isolation assistance method in accordance with the present embodiment. FIGS. 9 and 10 illustrate examples of a screen displayed using the cell isolation assistance method in accordance with the present embodiment. Next, by referring to FIGS. 8-10, descriptions are given of the cell isolation assistance method in accordance with the first embodiment which is implemented by the system 1.

Upon the processes depicted in FIG. 8 being started, the system 1 first obtains settings for the cell isolation assistance method (step S11). In this case, the control apparatus 30 makes settings for the cell isolation assistance method on the basis of information input by the user using the input apparatus 34. For example, setting items may include the cell type of cells forming a biological tissue section T within the container 100, the name and concentration of a proteolytic enzyme in a solution S, the intervals between time-lapse image capturing operations performed by the image capturing apparatus 10, and information on what parameter is to be used as an indicator of cell isolation (cell count, contrast).

Next, the system 1 obtains images in accordance with the settings made in step S11 (step S12). In this case, the control apparatus 30 transmits, to the image capturing apparatus 10, an image capturing instruction for performing image capturing at the intervals set in step S11; the image capturing apparatus 10, upon receipt of the image capturing instruction, images cells isolated from the biological tissue section T within the container 100; and the control apparatus 30 receives, from the image capturing apparatus 10, cell images, i.e., images generated by the image capturing apparatus 10.

Then, the system 1 calculates, from the images obtained in step S12, the contrast of the images and the number of cells isolated from the biological tissue section T (step S13). In this case, the control apparatus 30 calculates both the cell count and the contrast by analyzing the images. In addition, the control apparatus 30 associates the calculated cell count and contrast with an image capturing time and stores the same in the auxiliary storage apparatus 33 as indicators of the cell isolation.

Upon the cell count and the contrast being calculated, the system 1 displays graphs on the output apparatus 35 (step S14). In this case, the control apparatus 30 reads, as a history of the indicators, the cell count and the contrast calculated in step S13 from the auxiliary storage apparatus 33 together with the image capturing time. Then, the control apparatus 30 visualizes temporal changes in the indicators of the cell isolation on the basis of the history of the indicators that has been read. In particular, as depicted in FIG. 9, a graph G1 indicating a temporal change in the cell count and a graph G2 indicating a temporal change in the contrast are created and displayed on a screen 35a. Hence, the user can easily grasp the progress of the cell isolation by referring to the graphs.

In addition, the system 1 displays a latest image (step S15). In this case, as depicted in FIG. 9, the control apparatus 30 displays an image M1 captured at the most recent imaging time point, among the cell images received from the image capturing apparatus 10, on the screen 35a together with the graphs G1 and G2. In this way, the image can be checked without taking the container 100 out of the incubator 20 unlike in the prior art, in which such an image would need to be checked by taking the container 100 out of the incubator 20. Using the conventional image-based progress evaluation in combination with the quantitative progress evaluation using the graphs allows the user to confidently decide that cell isolation has been completed.

Furthermore, the system 1 monitors user input (step S16). When detecting input (YES in step S16), the system 1 displays a selection image (step S17). In step S17, the control apparatus 30 specifies a position on the graph G1 or G2 that has been selected by the user using an arrow A, selects, as a selection image M2, an image corresponding to an image capturing time indicated by the position, and displays the selection image M2 in, for example, a pop-up manner as depicted in FIG. 10. Displaying an image corresponding to a selected position on a graph like this allows the user to check an image corresponding to any time in the cell isolation process. Accordingly, by comparing the latest image M1 with the selection image M2, the progress of the cell isolation can be checked from the difference between the images. When the value of the cell count or the contrast value exhibits a possibility of occurrence of an abnormality at a particular time, the user can check the cell image at that time so as to check whether an abnormality has occurred. When an abnormality has occurred, the user can take an action such as canceling the cell isolation.

The system 1 repeats the processes until an end instruction is given by the user (step S18). As described above, by implementing the cell isolation assistance method in accordance with the present embodiment indicated in FIG. 8, the system 1 can provide the user with information for objectively deciding the progress of the cell isolation. In this way, the user can reliably and immediately perceive the completion of cell isolation. Accordingly, the system 1 can reliably assist in cell isolation while suppressing damage to cells.

Second Embodiment

Figure 11:
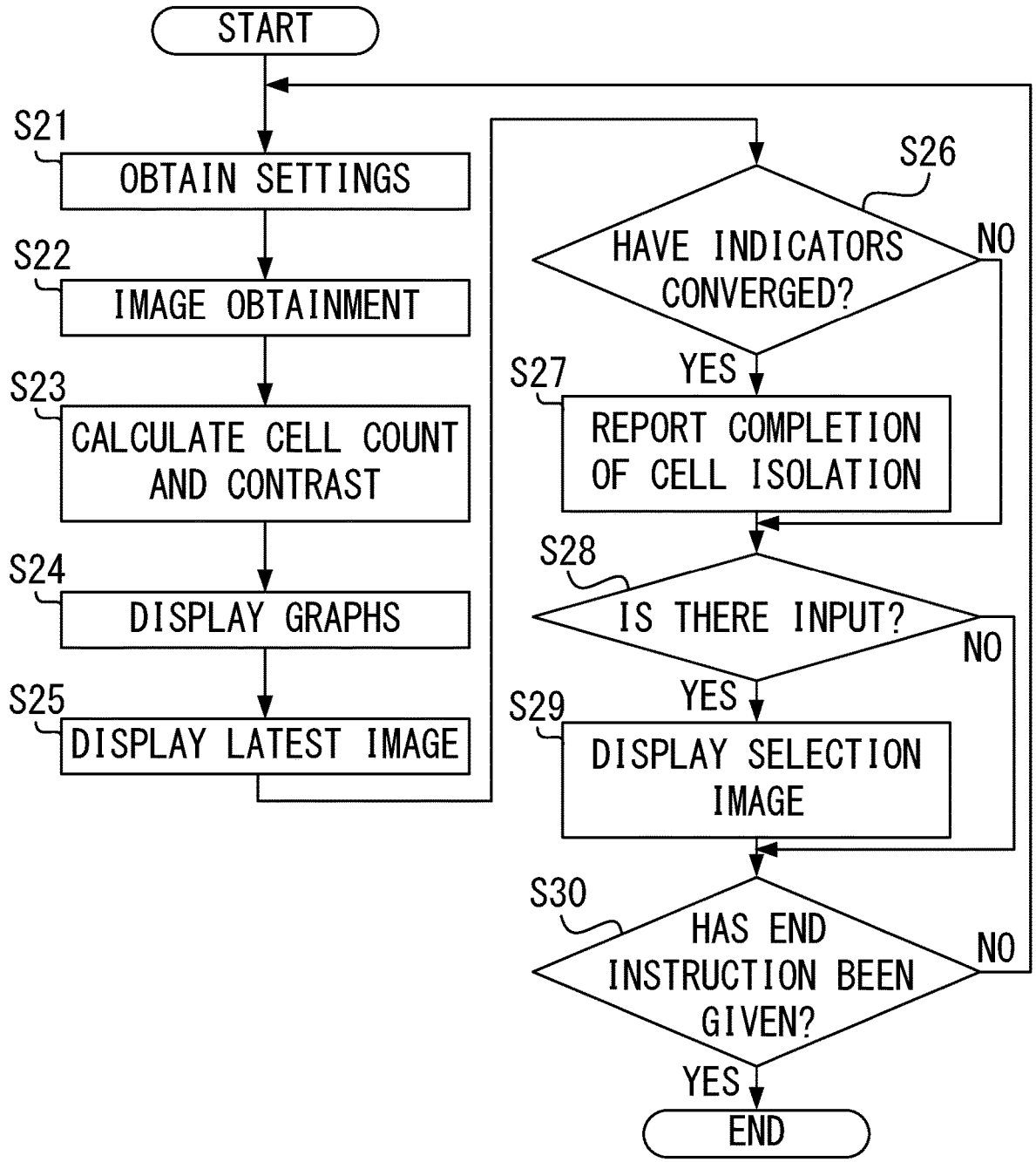
FIG. 11 is a flowchart for a cell isolation assistance method in accordance with a second embodiment.
Figure 12:
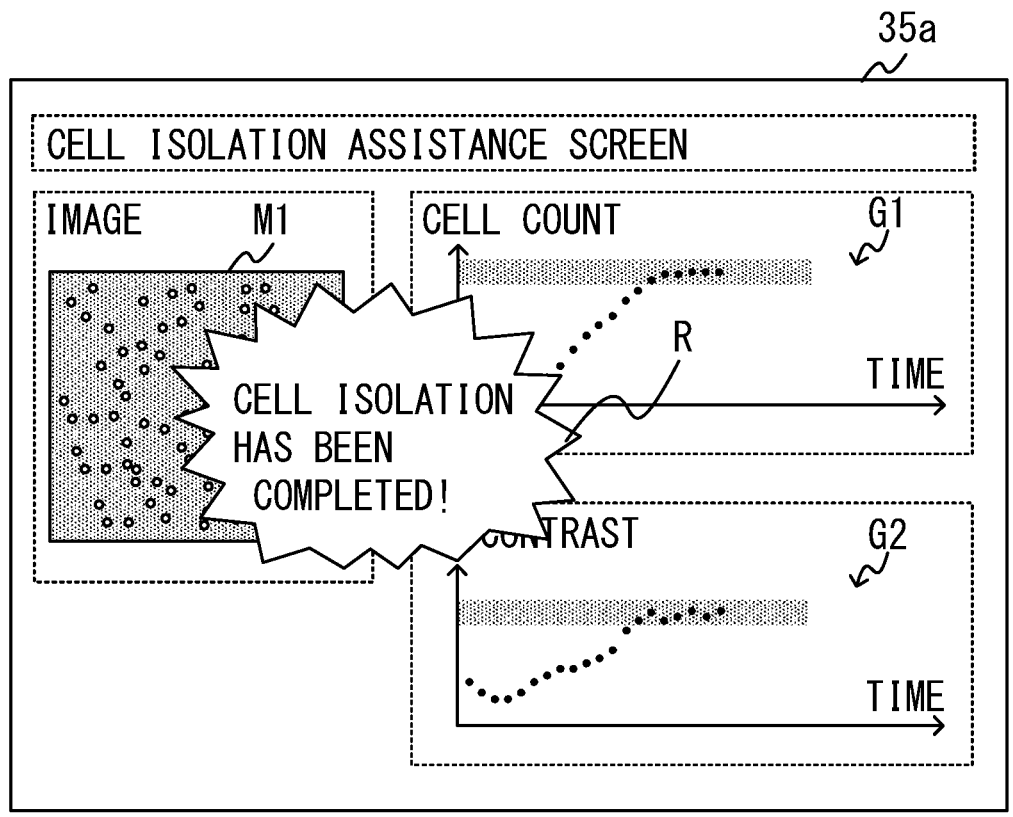
FIG. 12 illustrates an example of a screen displayed using a cell isolation assistance method in accordance with a second embodiment.

FIG. 11 is a flowchart for a cell isolation assistance method in accordance with the present embodiment. FIG. 12 illustrates an example of a screen displayed using the cell isolation assistance method in accordance with the present embodiment. Next, by referring to FIGS. 11 and 12, descriptions are given of the cell isolation assistance method in accordance with the second embodiment which is implemented by the system 1. The cell isolation assistance method in accordance with the present embodiment is largely different from the cell isolation assistance method in accordance with the first embodiment in that the system 1 determines the completion of cell isolation and reports the same.

Upon the processes depicted in FIG. 11 being started, the system 1 first obtains settings for the cell isolation assistance method (step S21). The process of step S21 is similar to that of step S11. In step S21, however, information for deciding whether cell isolation has been completed may also be included as a setting item.

Next, the system 1 obtains images (step S22), calculates a cell count and a contrast from the obtained images as indicators of the cell isolation (step S23), and displays graphs and the latest image (steps S24 and S25). These processes are similar to those of steps S12-S15 in FIG. 8.

Then, the system 1 determines whether the indicators obtained in step S23 have converged (step S26). When determining that the indicators have converged, the system 1 reports the completion of the cell isolation (step S27). In step S26, the control apparatus 30 determines whether a temporal change in each indicator has converged. When determining that the temporal change in each indicator has converged, the control apparatus 30 determines that the cell isolation has been completed. That is, the control apparatus 30 determines whether the cell isolation has been completed on the basis of the temporal change in each indicator. In step S27, the control apparatus 30 reports the completion of the cell isolation on the basis of the result of the determination in step S26. More specifically, the control apparatus 30 may report the completion of the cell isolation by, for example, displaying the completion of the cell isolation on the screen 35a, as depicted in FIG. 12. In this way, the possibility of the user missing the completion of cell isolation will be reduced.

Furthermore, the system 1 monitors user input (step S28). When detecting input (YES in step S28), the system 1 displays a selection image (step S29). The processes of steps S28 and S29 are similar to those of steps S16 and S17.

The system 1 repeats the processes until an end instruction is given by the user (step S30). As described above, by implementing the cell isolation assistance method in accordance with the present embodiment which is depicted in FIG. 11, the system 1 can reliably assist in cell isolation while suppressing damage to cells, as in the case of implementing the cell isolation assistance method in accordance with the first embodiment. In the cell isolation assistance method in accordance with the present embodiment which is depicted in FIG. 11, moreover, the system 1 decides whether cell isolation has been completed. Hence, the user can be suppressed from carelessly missing the completion of the cell isolation.

The embodiments described above indicate specific examples to facilitate understanding of the invention, and the present invention is not limited to these embodiments. Some of the embodiments described above may be applied to other embodiments. Various modifications or changes can be made to the method and system for cell isolation assistance and the computer-readable medium without departing from the recitation in the claims.

In the examples indicated for the embodiments described above, both a cell count and a contrast are calculated as indicators of cell isolation. However, at least either a cell count or a contrast may be calculated. In the examples indicated for the second embodiment, it is determined whether cell isolation has been completed on the basis of a temporal change in each indicator. However, the progress status of cell isolation may be determined on the basis of a temporal change in the indicator. Completion of cell isolation is an example of the progress status of the cell isolation. Besides completion of cell isolation, for example, the progress status of cell isolation may be start of cell isolation. For example, it may be determined that cell isolation has started on the basis of the fact that a contrast has decreased and a cell count has increased.

The "progress status of cell isolation" herein means the proportion of cells isolated from a biological tissue section. Start and completion of cell isolation are examples of the progress status. In the examples indicated above, the progress status of cell isolation is calculated on the basis of a temporal change in an indicator (cell count, contrast). However, the progress status of cell isolation may be calculated on the basis of the degree of increase in a cell count with reference to the volume or area of a biological tissue section, the decree of increase or decrease in a contrast, or the degree of decrease in the volume or area of the biological tissue section. For example, the method for reporting a progress status may be a method in which completion is reported in a pop-up manner as depicted in FIG. 12, a method in which the progress status is represented using text data, such as "PROGRESS RATE: n %," or a method in which the progress status is displayed using a circle graph or the like on a screen.

In addition to visualizing an indicator and reporting a progress status, information pertaining to ongoing cell isolation may be provided for the user by using various methods. For example, a graph indicating the degree of increase in a cell count with reference to the mass or area of a biological tissue section or the degree of decrease in the area of the biological tissue section may be displayed. Alternatively, an ideal cell-isolation curve graph (graph for cell count and time or for contrast and time) created by the user may be displayed overlapping a graph indicating the actual cell count (contrast), and the ratio of the actual cell count (contrast) to the cell count (contrast) on the ideal curve may be displayed. In addition, an image captured at a particular time point designated in advance by the user or the value of each indicator obtained at the particular time point may be displayed. The user may repeat experiments to obtain the relationship between the cell count or contrast and the time required for cell isolation in the user environment, i.e., each individual user can create an ideal curve. The time point designated in advance by the user may be six hours or twelve hours after the start of cell isolation, i.e., the user may set any value.

In the examples indicated for the embodiments described above, a contrast is calculated as an indicator of cell isolation. For example, the contrast may be a Michelson contrast $[(Lmax-Lmin)/(Lmax+Lmin)]$ or a contrast ratio $Lmax/Lmin$. With respect to the Michelson contrast, $Lmax$ and $Lmin$ indicate the highest value and the lowest value of the luminance values in an image. With respect to the contrast ratio, $Lmax$ indicates a luminance obtained when white is displayed, and $Lmin$ indicates a luminance obtained when black is displayed. The examples of the contrast are not limited to these. The contrast in the present invention is not particularly limited as long as the contrast of an image is represented. For example, the contrast may be calculated using Brenner Gradient. In Brenner Gradient, the squares of the differences in pixel value between neighboring pixels are integrated within a certain region.

In the examples indicated for the second embodiment, the completion of cell isolation is reported. However, when the progress status of cell isolation is determined, the progress status of the cell isolation may be reported on the basis of the result of the determination of the progress status of the cell isolation. Although screen displaying is presented herein as a specific example of the reporting method, the reporting method is not limited to screen displaying, as long as information can be conveyed to the user. For example, information may be reported using sounds or vibrations. Furthermore, for example, when it is decided that cell isolation has been completed, the control apparatus 30 may transmit mail reporting the completion of the cell isolation to a mail address registered in advance.

In addition, the completion of cell isolation may be reported by sending a report to a smartphone or a tablet computer, i.e., a portable terminal owned by a user, through wireless communication. Accordingly, the user can be notified of the completion of cell isolation even without staying in the vicinity of the incubator or staying in the operation room. For example, the wireless communication may be performed using WiFi®, LTE®, NFC®, or Bluetooth®. The report may be sent via any network such as PAN, LAN, or WAN.

Figure 13:
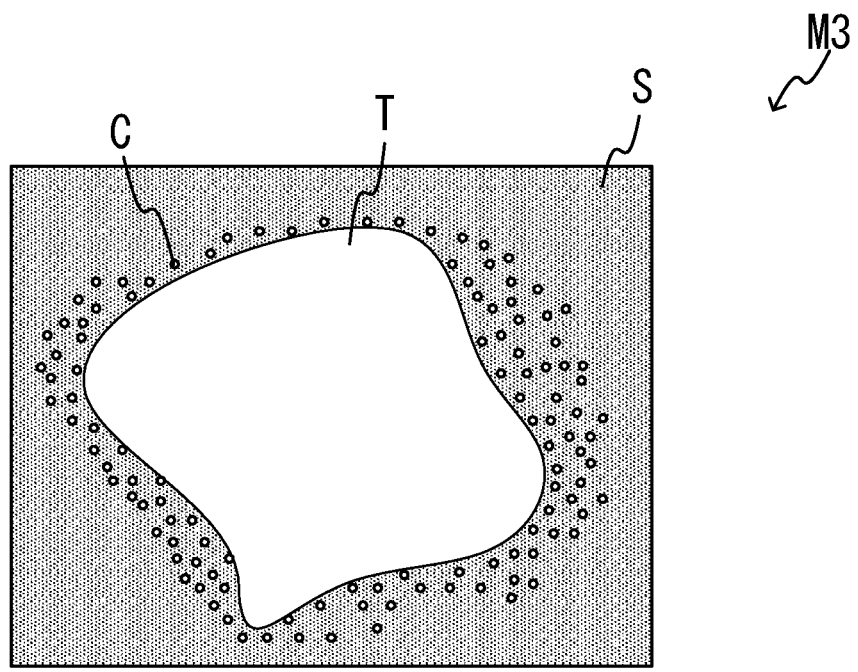
FIG. 13 illustrates another example of an image obtained by an image capturing apparatus.

In the examples indicated for the embodiments described above, a portion of a biological tissue section is imaged. However, the entirety of a biological tissue section T may be imaged as indicated by an image M3 depicted in FIG. 13. In this case, the image capturing apparatus is preferably provided with a line sensor so as to scan the biological tissue section T. When imaging a biological tissue section T that is larger than the field of view of the image capturing apparatus, image capturing may be performed a plurality of times by moving the field of view to a plurality of positions on the biological tissue section T, and a plurality of obtained images may be combined to provide an image of the entirety of the biological tissue section T. In addition, the image capturing apparatus may be mounted with a plurality of image capturing units, in particular, an image capturing unit that can image the entirety of a biological tissue section T and image capturing units that image portions of the biological tissue section T. The flow of processes for imaging the entirety of a subject is similar to the flows indicated by the flowcharts in FIGS. 5, 8, and 11, and descriptions thereof are omitted herein.

Variations

Figure 14:
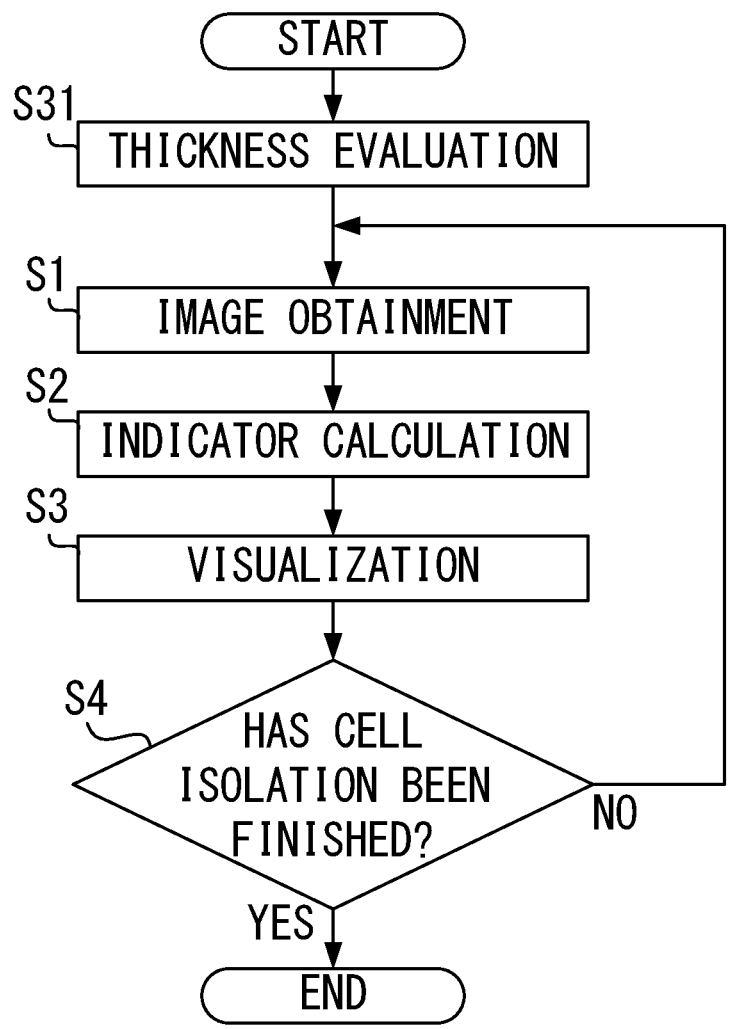
FIG. 14 is a flowchart for a cell isolation assistance method in accordance with a variation.

In the embodiments described above, a portion of a biological tissue section is imaged to observe cell isolation. Doing so is advantageous especially when cell isolation progresses almost uniformly at every portion of the section. In such a situation, as in the embodiments described above, an image of a portion of the section that the user thinks the most suitable to be imaged may be captured. As indicated in FIG. 14, before the image obtainment process (step S1) is performed, a thickness evaluation may be made for a biological tissue section by obtaining an image of the entirety of the biological tissue section (step S31).

With respect to a biological tissue section that exhibits large variations in thickness according to portions thereof, the progress of isolation will differ according to portions. In particular, with reference to an equal surface area, a longer time will be required for isolation as the thickness or the amount (volume) of cells to be leached increases, and a shorter time will be required for isolation as the thickness or the amount (volume) of cells to be leached decreases. Thus, a biological tissue section will typically be prepared such that the section does not exhibit large variations in thickness according to portions thereof. However, an inexperienced operator may prepare a biological tissue section that exhibits large variations in thickness according to portions thereof. An indicator calculated by imaging a portion of the biological tissue section that exhibits variations in thickness according to portions thereof may not be sufficiently reliable as an indicator of cell isolation.

In step S31, accordingly, the thickness evaluation may be performed for the biological tissue section in advance through a process in which the entirety of the biological tissue section is imaged and focusing is checked. In particular, the focusing should be good at thin portions and bad at thick portions. When the focusing is uniform over the entirety of a biological tissue section, an evaluation that the thickness is sufficiently uniform can be given. Alternatively, instead of imaging the entirety of a biological tissue section, images of different portions of the biological tissue section may be captured by moving the image capturing unit, and the images of various portions may be combined to provide an image of the entirety of the biological tissue section. The reliability of cell isolation may be calculated using a result of the thickness evaluation for the biological tissue section and displayed.

Figure 15:
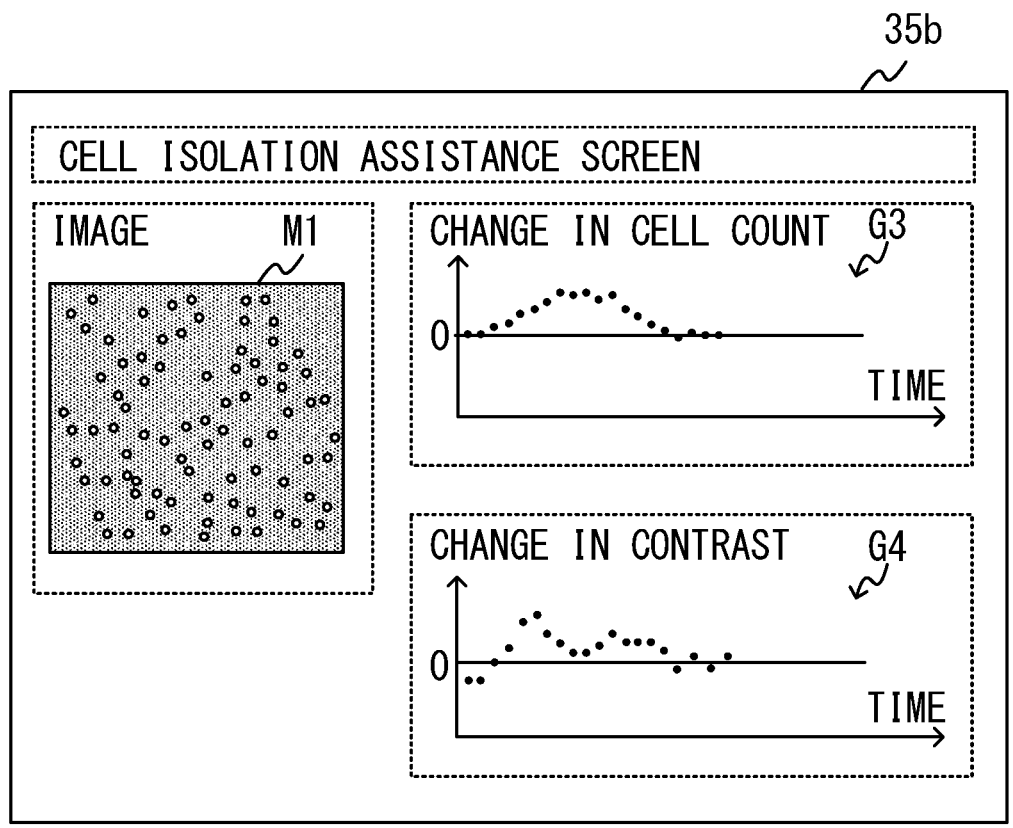
FIG. 15 illustrates another example of a screen displayed using a cell isolation assistance method in accordance with a second embodiment.

In the examples indicated for the embodiments described above, a graph obtained by plotting values for an indicator at various times is displayed to visualize a temporal change in the indicator. However, the method for visualizing a temporal change in an indicator is not limited to these examples. For example, graphs each provided by plotting values obtained by time-differentiating an indicator at various times (graphs G3 and G4) may be displayed on a screen 35b as depicted in FIG. 15. The graphs may be line graphs. In this case, the control apparatus 30 may determine whether a value has converged to 0, and may determine that cell isolation has been completed when the value has converged to 0. The difference in the pixel value of an image between different imaging times may be used as an indicator. As with the time-differentiations of the cell count and the contrast, a temporal change in the difference in the pixel value of the image can be used as a standard for deciding that cell isolation has been completed. In particular, as cell isolation progresses, the difference in the pixel value decreases because motions of the biological tissue section and the cells in the image decrease. Meanwhile, instead of the number of isolated cells, the area of the biological tissue section in the image may be used as an indicator. The method for determining an increase or decrease in the area of the section from images may be a method wherein the difference in contrast between two images captured at different imaging time points is determined, or a method wherein a learning-completed model that has performed learning to determine the area of a section through machine learning is used. The area of a section is a suitable indicator for the same reason as a cell count. When an image of the entirety of a section can be captured, the area of the section will be an excellent indicator because the inflow and outflow of cells to/from the field of view are unlikely to occur, unlike in the case of isolated cells.

The method for visualizing a temporal change in an indicator may be a method wherein a history of a cell count or a history of the numerical value of a contrast is displayed in addition to graphs, a method wherein a cell count or the numerical value of a contrast is updated on an as-needed basis and displayed, or a method wherein color vision information is superimposed on an image captured in real time. In particular, color vision information of yellow may be superimposed when cell isolation is almost finished, and color vision information of red may be superimposed when cell isolation has been finished. In this way, the temporal change in the indicator is visualized by the change in the color.

The system 1 can also be used to monitor culture cells placed in the incubator 20. Using the system 1 so as to monitor culture cells allows both the step for preparing for cell culturing and the step for performing the cell culturing to be carried out using the same system. In this way, the system 1 can be used efficiently, thereby attaining high efficiencies in terms of both cost and tasks. In particular, after finishing cell isolation within the incubator 20, an operator takes a container out of the incubator 20 and uses a centrifugal separator or the like so as to separate or extract isolated cells from other materials or wash the same. The number of extracted cells is counted by causing the cells to pass through, for example, a flow cell meter. Afterward, the cells are seeded within a culture container containing a culture solution. Then, the culture container containing the isolated cells is set within the incubator 20, and the culture cells are monitored using the system 1.

Enzyme levels, cell types, types of biological tissue sections, and section volumes may be stored in a database so as to be associated with times required for cell isolation and cell counts that can be obtained. For example, a user, before starting cell isolation, may input the volume and type of a biological tissue section to the database, so that information on an estimated time required for the cell isolation to be finished can be read in advance and grasped. After the cell isolation is finished, the user may add information to the database by inputting an experimental result thereto. In this way, the user can estimate in advance a time required for cell isolation and a cell count that can be obtained, so that the cell isolation can be performed efficiently.

Figure 16:
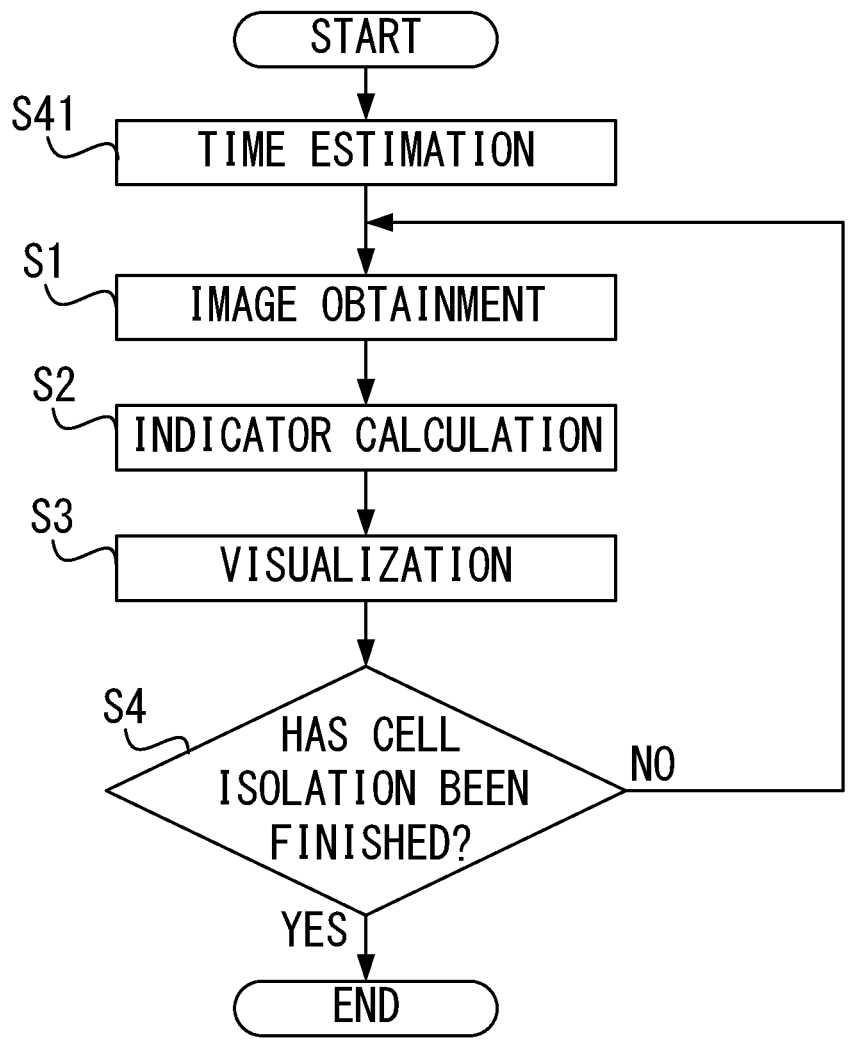
FIG. 16 is a flowchart for a cell isolation assistance method in accordance with another variation.

Recording a time that was spent for cell isolation together with parameters such as cell type and enzyme level allows data for creating a learning model for estimating a time required for cell isolation to be provided. By learning the relationship between the parameters and time by using the collected data, a learning model for estimating a time required for cell isolation can be produced. The learning model in accordance with the present embodiment may be created using, for example, a neural network. For example, the learning model may output a time that will be required for cell isolation from a biological tissue section, in response to input of a cell type, an enzyme level, and the volume and mass of a tissue section. For example, as indicated in FIG. 16, before starting cell isolation from any biological tissue section, the user may select a learning model pertaining to a corresponding cell type so as to estimate a time required for the cell isolation in advance (step S41). The learning model may be downloaded to the control apparatus from an external storage apparatus, an external terminal, or a cloud, or may be stored in the control apparatus in advance. By inputting information such as the cell type, the enzyme level, and the volume and mass of the tissue section to the selected learning model, the user can start the cell isolation, with information on a time that will be required for the cell isolation having been obtained using the learning model. Meanwhile, causing the learning model to learn cell counts each obtained after the end of cell isolation as output information allows an estimated cell count to be output. By estimating as described above a time required for cell isolation and a cell count that can be obtained, the user can easily plan the entirety of an experimental protocol, including cell culturing. The user can cause the learning model that was used to learn a result of cell isolation obtained by the user.

Appendix 1. A method for assisting in cell isolation from a biological tissue section, the method comprising steps for:
  obtaining cell images that are each an image of cells isolated from the biological tissue section, the biological tissue section being soaked in a solution containing an enzyme;
  calculating, from the cell images, at least either a number of the cells isolated from the biological tissue section or a contrast of the cell images as an indicator of the cell isolation from the biological tissue section; and
  visualizing a temporal change in the indicator on the basis of a history of the indicator.

Appendix 2. The method of appendix 1, wherein
  the step for calculation from the images includes a step for calculating both the number of the cells and the contrast of the cell images as indicators.

Appendix 3. A system comprising:
  an image capturing apparatus that images a biological tissue section soaked in a solution containing an enzyme; and
  a control apparatus that obtains, from the image capturing apparatus, cell images that are each an image of cells isolated from the biological tissue section, wherein
    the control apparatus
    calculates, from the obtained cell images, at least either a number of the cells isolated from the biological tissue section or a contrast of the cell images as an indicator of the cell isolation from the biological tissue section, and
    visualizes a temporal change in the calculated indicator on the basis of a history of the indicator.

Appendix 4. The system of appendix 3, wherein
  the calculation from the cell images includes calculating as indicators.

Appendix 5. A non-transitory computer-readable medium having recorded therein a program for causing a computer to perform a process for:
  obtaining cell images that are each an image of cells isolated from a biological tissue section soaked in a solution containing an enzyme;
  calculates, from the obtained cell images, at least either a number of the cells isolated from the biological tissue section or a contrast of the cell images as an indicator of the cell isolation from the biological tissue section, and
  visualizing a temporal change in the calculated indicator on the basis of a history of the indicator.

Appendix 6. The computer-readable medium of appendix 5, wherein
  the calculation from the cell images includes calculating both the number of the cells and the contrast of the cell images as indicators.

What is claimed is:

1. A method for assisting in cell isolation from a biological tissue section, the method comprising:
  obtaining cell images that each include an image containing cells isolated from the biological tissue section, the biological tissue section being soaked in a solution containing an enzyme, and the cell images being images obtained during an isolation process when cells are being isolated from the biological tissue section;
  calculating, from the cell images, a number of the cells isolated from the biological tissue section as an indicator of the cell isolation from the biological tissue section; and
  visualizing a temporal change in the indicator on the basis of a history of the indicator.

2. The method according to claim 1, wherein the obtained cell images that further include the image containing at least a portion of the biological tissue section.

3. A method for assisting in cell isolation from a biological tissue section, the method comprising:
  obtaining cell images that each include an image containing cells isolated from the biological tissue section, the biological tissue section being soaked in a solution containing an enzyme, and the cell images being images obtained during an isolation process when cells are being isolated from the biological tissue section;
  calculating, from the cell images, a contrast of the cell images as an indicator of the cell isolation from the biological tissue section; and
  visualizing a temporal change in the indicator on the basis of a history of the indicator.

4. The method of claim 3, further comprising:
  calculating, from the cell images, a number of the cells isolated from the biological tissue section as an indicator of the cell isolation from the biological tissue section.

5. The method of claim 3, wherein
  the visualizing the temporal change in the indicator includes displaying a graph indicating the temporal change in the indicator.

6. The method of claim 5, further comprising:
  displaying an image captured at a most recent imaging time point among the cell images.

7. The method of claim 5, further comprising:
displaying, among the cell images, an image that corresponds to an imaging time indicated by a selected position on the graph.

8. The method of claim 3, further comprising:
determining a progress status of the cell isolation on the basis of a temporal change in the indicator; and
reporting the progress status of the cell isolation on the basis of a result of the determination of the progress status of the cell isolation.

9. The method of claim 8, wherein
the determining the progress status of the cell isolation includes determining whether the cell isolation has been completed on the basis of the temporal change in the indicator, and
the reporting the progress status of the cell isolation includes reporting completion of the cell isolation on the basis of the result of the determination of the progress status of the cell isolation.

10. The method of claim 9, wherein
the determining whether the cell isolation has been completed includes
determining whether the temporal change in the indicator has converged, and
determining that the cell isolation has been completed when it is determined that the temporal change in the indicator has converged.

11. The method of claim 8, wherein
the reporting the progress status of the cell isolation on the basis of the result of the determination of the progress status of the cell isolation is performed through wireless communication with a terminal.

12. The method of claim 8, wherein
the reporting the progress status of the cell isolation includes visually displaying an image or text indicating the progress status of the cell isolation.

13. The method of claim 3, further comprising:
estimating a time required to complete the cell isolation by using a database or a learning-completed model, and displaying the estimated time.

14. The method according to claim 3, wherein
the cell images include a plurality of cell images obtained at different times in the isolation process, and
the indicator is calculated from each of the plurality of cell images.

15. The method according to claim 3, wherein the cell images include an image obtained by imaging the biological tissue section soaked in the solution containing an enzyme.

16. The method according to claim 3, wherein the obtained cell images that further include the image containing at least a portion of the biological tissue section.

17. A system comprising:
an image capturing apparatus configured to image cells isolated from a biological tissue section soaked in a solution containing an enzyme; and
a control apparatus configured to obtain, from the image capturing apparatus, cell images that each include an image containing the cells isolated from the biological tissue section, and the cell images being images obtained during an isolation process when cells are being isolated from the biological tissue section,
wherein the control apparatus is configured to:
calculate, from the obtained cell images, a number of the cells isolated from the biological tissue section as an indicator of the cell isolation from the biological tissue section, and
visualize a temporal change in the calculated indicator on the basis of a history of the indicator.

18. The system of claim 17, wherein
the control apparatus is configured to
calculate, from the obtained cell images, a contrast of the cell images as an indicator of the cell isolation from the biological tissue section.

19. The system according to claim 17, wherein the obtained cell images that further include the image containing at least a portion of the biological tissue section.

20. A system comprising:
an image capturing apparatus configured to image cells isolated from a biological tissue section soaked in a solution containing an enzyme; and
a control apparatus configured to obtain, from the image capturing apparatus, cell images that each include an image containing the cells isolated from the biological tissue section, and the cell images being images obtained during an isolation process when cells are being isolated from the biological tissue section,
wherein the control apparatus is configured to:
calculate, from the obtained cell images, a contrast of the cell images as an indicator of cell isolation from the biological tissue section, and
visualize a temporal change in the calculated indicator on the basis of a history of the indicator.

21. The system according to claim 20, wherein the obtained cell images that further include the image containing at least a portion of the biological tissue section.

22. A non-transitory computer-readable medium having recorded therein a program for causing a computer to perform a process for:
obtaining cell images that each include an image containing cells isolated from a biological tissue section soaked in a solution containing an enzyme, and the cell images being images obtained during an isolation process when cells are being isolated from the biological tissue section;
calculating, from the obtained cell images, a number of the cells isolated from the biological tissue section as an indicator of cell isolation from the biological tissue section; and
visualizing a temporal change in the calculated indicator on the basis of a history of the indicator.

23. The computer-readable medium of claim 22, having recorded therein a program for causing a computer to perform a process for:
calculating, from the obtained cell images, a contrast of the cell images as an indicator of the cell isolation from the biological tissue section.

24. The non-transitory computer-readable medium according to claim 22, wherein the obtained cell images that further include the image containing at least a portion of the biological tissue section.

25. A non-transitory computer-readable medium having recorded therein a program for causing a computer to perform a process for:
obtaining cell images that each include an image containing cells isolated from a biological tissue section soaked in a solution containing an enzyme, and the cell images being images obtained during an isolation process when cells are being isolated from the biological tissue section;
calculating, from the obtained cell images, a contrast of the cell images as an indicator of cell isolation from the biological tissue section; and visualizing a temporal change in the calculated indicator on the basis of a history of the indicator.

26. The non-transitory computer-readable medium according to claim 25, wherein the obtained cell images that further include the image containing at least a portion of the biological tissue section.

* * * * *